United States Patent [19]
Vonderhagen et al.

[11] Patent Number: 5,962,624
[45] Date of Patent: Oct. 5, 1999

[54] ENZYMATIC SYNTHESIS OF POLYESTERS

[75] Inventors: Anja Vonderhagen, Duesseldorf, Germany; Jeffrey A. Gates, West Chester, Ohio; Karlheinz Hill, Erkrath, Germany; Martin Lagarden, Duesseldorf, Germany; Holger Tesmann, Juechen, Germany

[73] Assignee: Hendel Kommanditgesellschaft auf Aktien, Duesseldorf, Germany

[21] Appl. No.: 09/038,994

[22] Filed: Mar. 10, 1998

[51] Int. Cl.$^6$ .............................. C08G 63/78; C12N 9/00
[52] U.S. Cl. ......................... 528/274; 435/183; 524/700; 524/704; 524/770
[58] Field of Search ........................... 528/274; 435/183; 524/700, 704, 770

[56] References Cited

U.S. PATENT DOCUMENTS 5,478,910  12/1995  Russell et al. ........................... 528/274

OTHER PUBLICATIONS

Mezoul, et al., "Enzyme–Catalyzed Synthesis Of Aliphatic Polyesters In Organic Media: Study Of Transesterification Equilibrium Shift And Characterization Of Cyclic Compounds", Journal Of Polymer Science, Part A: Polymer Chemistry, vol. 33, John Wiley & Sons, Inc., 1995, pp. 2691–2698.

Okumura, et al., "Synthesis Of Ester Oligomer By *Aspergillus niger* Lipase", Agric. Biol. Chem., 48 (11), 1984, pp. 2805–2808.

Wu, et al., "Lipase–Catalyzed Polyester Synthesis", Biotechnology Techniques, vol. 10., No. 10, Oct., 1996, pp. 793–798.

Kobayashi, et al., "Dehydration Polymerization In Aqueous Medium Catalyzed By Lipase", Chemistry Letters 1997, The Chemical Society of Japan, p. 105.

*Primary Examiner*—Samuel A. Acquah
*Attorney, Agent, or Firm*—Wayne C. Jaeschke; John E. Drach; Joanne Mary Fobare Rossi

[57] ABSTRACT

A linear polyester is made by a process reacting polyols comprising at least two primary alcohol groups and at least one secondary alcohol or amino group and a dicarboxylic acid or a dicarboxylic acid ester in the presence of an effective amount of a lipase derived from *Candida cylindracea, Candida lipolytica, Candida rugosa, Candida antarctica, Candida utilis, Chromobacterium viscosum, Geotrichum viscosum, Geotrichum candidum, Mucor javanicus, Mucor miehei, Porcine pancreas*, Pseudomonas species, specifically *Pseudomonas fluorescens, Pseudomonas cepacia, Pseudomonas pseudoalkaligenes, Pseudomonas alkaligenes*, Thermomyces species, *Rhizopus arrhizus, Rhizopus delemar, Rhizopus niveus, Rhizopus oryzae, Rhizopus javanicus, Aspergillus niger, Penicillium roquefortii, Penicillium camembertii* or an esterase derived from Bacillus species, specifically *Bacillus thermoglucosidasius; Mucor miehei*, Horse liver, *Saccharomyces cerevisiae*, Pigs liver or combinations thereof. The secondary OH or amino group of the polyol moiety is unreacted.

21 Claims, No Drawings

ENZYMATIC SYNTHESIS OF POLYESTERS

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

Polyesters based on polyols and dicarboxylic acids are useful in formulating products such as skin cremes, cosmetics and the like. In such formulations, the polyesters normally function as thickeners or softeners. Polyesters prepared from polyols comprising at least two primary alcohol groups and at least one secondary alcohol or amino group and a dicarboxylic acid wherein the secondary OH or amino group of the polyol moiety is free or unesterified have surface active properties. The difficulty normally encountered in the preparation of such polyesters is the danger that because the polyol is multifunctional, the polyester would be non-linear and thus the reaction mixture would tend to gel before the degree of conversion reaches acceptable levels.

SUMMARY OF THE INVENTION

The surprising discovery has been made that linear polyesters are made by reacting a polyol comprising at least two primary alcohol groups and at least one secondary alcohol or amino group and a dicarboxylic acid or an ester of a dicarboxylic acid in the presence of an effective amount of a lipase derived from *Candida cylindracea, Candida lipolytica, Candida rugosa, Candida antarctica, Candida utilis, Chromobacterium viscosum, Geotrichum viscosum, Geotrichum candidum, Mucor javanicus, Mucor miehei, Porcine pancreas*, Pseudomonas species, specifically *Pseudomonas fluorescens, Pseudomonas cepacia, Pseudomonas pseudoalkaligenes, Pseudomonas alkaligenes*, Thermomyces species, *Rhizopus arrhizus, Rhizopus delemar, Rhizopus niveus, Rhizopus oryzae, Rhizopus javanicus, Aspergillus niger, Penicillium roquefortii, Penicillium camembertii* or an esterase derived from Bacillus species, specifically *Bacillus thermoglucosidasius; Mucor miehei*, Horse liver, *Saccharomyces cerevisiae*, Pigs liver. The use of the enzymes according to the invention allows the secondary alcohol or amino functionalities on the polyol moiety to remain substantially unesterified so that the polyester is linear. The process according to the invention can be carried out in the presence or in the absence of a solvent. The process according to the invention also allows the formation of polymer chain lengths as a function of time.

BRIEF DESCRIPTION OF THE SEVERAL VIEWS OF THE DRAWING

Not Applicable.

DETAILED DESCRIPTION OF THE INVENTION

The polyesterification process according to the invention can be carried out using polyols comprising at least two primary alcohol groups and at least one secondary alcohol or amino group and a dicarboxylic acid or a diester thereof. Any polyol comprising at least two primary alcohol groups and at least one secondary alcohol or amino group can be used. Preferably the polyol comprises up to 6 C-atoms and up to 6 OH— or $NH_2$-groups. Most preferred polyols are glycerol, sorbitol, sorbitan, trimethylolpropan, pentaerythritol and 2-amino-1,3-propanediol. Oligomers, for example, dimers, trimers, tetramers, pentamers and/or hexamers, of said polyols can also be used. Even mixtures of monomeric polyols and oligomers can be used. Any dicarboxylic acid, the corresponding mono- or diester can be used. Therefore, any aliphatic, substituted aliphatic, aromatic, or substituted aromatic dicarboxylic acid or ester known to those skilled in the art can be used. Examples of aliphatic dicarboxylic acids include, but are not limited to, oxalic, malonic, succinic, adipic, azelaic, dodecanedioc, brassylic acids and $C_{36}$ dimer acid and the like. Examples of aromatic dicarboxylic acids include, but are not limited to, phthalic, iso-phthalic and, terephthalic acids and the like. Examples of substituted dicarboxylic acids are amino diacids and hydroxy diacids such as tartaric acid. Any ester of the above-mentioned dicarboxylic acids can be used in the process according to the invention such as, for example, $C_{1-22}$ alkyl esters and phenolic esters. It is preferred to use esters of low-volatile alcohols, such as for example methanol, ethanol, propanol, iso-propanol and butanol.

The enzymes that can be used in the process according to the invention are selected from the group consisting of a lipase derived from *Candida cylindracea, Candida lipolytica, Candida rugosa, Candida antarctica, Candida utilis, Chromobacterium viscosum, Geotrichum viscosum, Geotrichum candidum, Mucor javanicus, Mucor miehei, Porcine pancreas*, Pseudomonas species, specifically *Pseudomonas fluorescens, Pseudomonas cepacia, Pseudomonas pseudoalkaligenes, Pseudomonas alkaligenes*, Thermomyces species, *Rhizopus arrhizus, Rhizopus delemar, Rhizopus niveus, Rhizopus oryzae, Rhizopus javanicus, Aspergillus niger, Penicillium roquefortii, Penicillium camembertii* or an esterase derived from Bacillus species, specifically *Bacillus thermoglucosidasius; Mucor miehei*, Horse liver, *Saccharomyces cerevisiae*, Pigs liver. Any one or a combination of such enzymes can be used. The choice of enzyme will depend upon the nature of the polyesterification reaction and will be readily ascertainable by those of ordinary skill in the art. The amount of enzyme used in the process according to the invention is an amount effective to catalyze the polyesterification reaction to achieve a particular conversion and molecular weight. Preferred enzymes include the lipase derived from *Rhizomucor miehei, Candida antarctica* B, *Mucor miehei, Penicillium camembertii, Rhizopus niveus, Rhizopus javanicus*, Pseudomanas species and *Aspergillus niger*. Especially preferred enzymes are NOVOZYM® 388 L (*Rhizomucor miehei* lipase, free), LIPOZYM® IM (*Rhizomucor miehei* lipase, immobilized), NOVOZYM® 735 L (*Candida antarctica* A Lipase, free), NOVOZYM® 525 L (*Candida antarctica* B Lipase, free) NOVOZYM® 435 (*Candida antarctica* B Lipase, immobilized), each of which is a trademark product of Novo Nordisk, Denmark. Also preferred are Lipase G (*Penicillium camembertii*, Amano), Lipase PS and AK (Pseudomonas sp., Amano), Lipase N (*Rhizopus niveus*, Amano) and Lipase FAP (*Rhizopus javanicus*, Amano). The most preferred enzymes are *Candida antarctica* B lipase, immobilized, available commercially as NOVOZYM® 435, and *Rhizomucor miehei* lipase, commercially available as LIPOZYM® IM.

The process according to the invention can be carried out in the presence or absence of a reaction solvent. If a solvent is used, ketones, secondary and tertiary alcohols are preferred. The preferred ketone is acetone. The process can be carried out at a temperature of from about 20° C. to about 90° C. and preferably at about 70° C. The process can be carried out at a pressure of from about 0.01 mbar to about 1013 mbar and preferably from about 10 mbar to about 600 mbar. The time required to carry out the process according to the invention will vary from about 1 hour to about 14 days with the preferred range from about 8 hours to about 7 days.

The molar ratio of diacid/polyol can vary from about 2/1 to about 0.5/1 and preferably from about 1.2/1 to about 0.8/1.

A particular advantage of the process according to the invention is molecular weight control relative to a process catalyzed by the standard catalysts. For example, oligoesters prepared according to the invention have an average of 2-3 repeat units after 8 hours. After 16 hours the oligomers have average repeat units of 5-6. After a defined period of time, a characteristic distribution of oligo- or polyesters are found. By using glycerol as polyol, the process according to the invention permits the synthesis of polyesters having molecular weights from 483 to 10000 as determined by GPC using polyethyleneglycol standards and up to 22000 as determined by GPC using polystyrene standards.

The following examples are meant to illustrate but not to limit the invention.

EXAMPLE 1

About 43 grams (0.2 moles) of dimethyl azelate was added to 18 grams (0.2 moles) of glycerol. The reaction was started by adding 7 grams of NOVOZYME® 435 and heating to 70° C. After 2 days on a rotary evaporator (pressure=400 mbar), the reaction was stopped by filtering the enzyme off and washing the residue with portions of ethanol. The solvent was removed in vacuo and 58 grams of product was obtained. More than 98% of the glycerin had reacted. The product was analyzed via GPC and found to contain a mixture of compounds I and II.

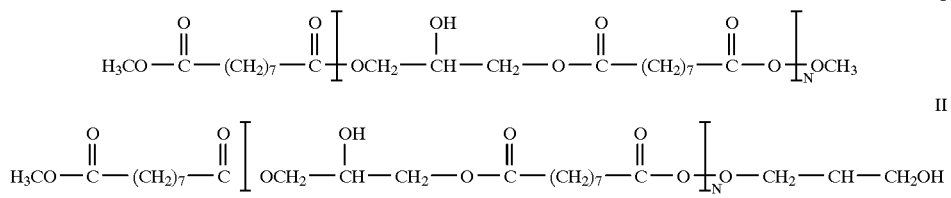

The degree of oligomerization was monitored as a function of reaction time and was found to be 1-2 after 8 hours, 2–5 after 24 hours and equal to or greater than 5 after 48 hours. The molecular weight average of the product mixture after 48 h was found to be about 2200 (calibration with polystyrene).

EXAMPLE 2

About 43 grams (0.2 moles) of dimethyl azelate was added to 18 grams (0.2 moles) of glycerol. The reaction was started by adding 1 gram of NOVOZYME® 435 and heating to 70° C. After 2 days on a rotary evaporator (pressure=150 mbar), the reaction was stopped by filtering the enzyme off and washing the residue with portions of ethanol. The solvent was removed in vacuo and 58 grams of product was obtained. More than 98% of the glycerin had reacted. The product was analyzed via GPC and found to contain a mixture of compounds I and II. The molecular weight average of the product mixture was found to be about 20,000 (calibration with polystyrene).

What is claimed is:

1. A process for making a linear polyester comprising reacting a polyol comprising at least two primary alcohol groups and at least one secondary alcohol or amino group and a dicarboxylic acid or a dicarboxylic acid ester in the presence of an effective amount of an enzyme derived from an organism selected from the group consisting of *Candida cylindracea, Candida lipolytica, Candida rugosa, Candida antarctica, Candida utilis, Chromobacterium viscosum, Geotrichum viscosum, Geotrichum candidum, Mucor javanicus, Mucor miehei, Porcine pancreas*, Pseudomonas species, Thermomyces species, *Rhizopus arrhizus, Rhizopus delemar, Rhizopus niveus, Rhizopus oryzae, Rhizopus javanicus, Aspergillus niger, Penicillium roquefortii, Penicillium camembertii* or an esterase derived from Bacillus species, *Mucor miehei*, Horse liver, *Saccharomyces cerevisiae*, Pigs liver and combinations thereof.

2. The process of claim 1 wherein the process is carried out in a solvent selected from the group consisting of a ketone, secondary alcohol and a tertiary alcohol.

3. The process of claim 2 wherein the solvent is acetone.

4. The process of claim 1 wherein the enzyme is *Candida antarctica* or *Rhizomucor miehei* lipase.

5. The process of claim 4 wherein the enzyme is *Candida antarctica* lipase immobilized.

6. The process of claim 1 wherein the molar ratio of diacid/polyol is from about 2/1 to about 0.5/1.

7. The process of claim 6 wherein the ratio is from about 1.2/1 to about 0.8/1.

8. The process of claim 1 wherein the process is carried out at a pressure of from about 0.01 mbar to about 1013 mbar.

9. The process of claim 8 wherein the pressure is from about 10 mbar to about 600 mbar.

10. The process of claim 1 wherein the dicarboxylic acid ester is dimethyl azelate or the dicarboxylic acid is adipic acid.

11. A linear polyester made by the process which comprises reacting a polyol comprising at least two primary alcohol groups and a cicarboxylic acid or a dicarboxylic acid ester in the presence of an effective amount of an enzyme derived from an organism selected from the group consisting of *Candida cylindracea, Candida lipolytica, Candida rugosa, Candica antarctica, Candida utilis, Chromobacterium viscosum, Geotrichum viscosum, Geotrichum candidum, Mucor javanicus, Mucor miehei, Porcine pancreas*, Pseudomonas species, Thermomyces species, *Rhizopus arrhizus, Rhizopus delemar, Rhizopus niveus, Rhizopus oryzae, Rhizopus javanicus, Aspergillus niger, Penicillium roquefortli, Penicillium camembertli*, Bacillus species, *Mucor miehei*, Horse liver, *Saccharomyces cerevisiae*, Pigs liver and combinations thereof.

12. The product of claim 11 wherein the process is carried out in a solvent selected from the group consisting of a ketone, secondary alcohol and a tertiary alcohol.

13. The product of claim 12 wherein the solvent is acetone.

14. The product of claim 11 wherein the enzyme is *Candida antarctica* or *Rhizomucor miehei* lipase.

15. The product of claim 14 wherein the enzyme is *Candida antarctica* immobilized.

16. The product of claim 11 wherein the molar ratio of diacid/polyol is from about 2/1 to about 0.5/1.

17. The product of claim 16 wherein the ratio is from about 1.2/1 to about 0.8/1.

18. The product of claim 11 wherein the process is carried out at a pressure of from about 0.01 mbar to about 1013 mbar.

19. The product of claim 18 wherein the pressure is from about 10 mbar to about 600 mbar.

20. The product of claim 11 wherein the dicarboxylic acid ester is dimethyl azelate or the dicarboxylic acid is azelaic acid.

21. The product of claim 11 wherein the dicarboxylic acid ester is dimethyl adipate or the dicarboxylic acid is adipic acid.

* * * * *